US00PP32672P2

(12) United States Plant Patent
van Dijk

(10) Patent No.: US PP32,672 P2
(45) Date of Patent: Dec. 22, 2020

(54) ***HYDRANGEA* PLANT NAMED 'HIRIV'**

(50) Latin Name: *Hydrangea macrophylla*
Varietal Denomination: HIRIV

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 16/873,393

(22) Filed: Apr. 4, 2020

Related U.S. Application Data

(60) Provisional application No. 62/974,253, filed on Nov. 21, 2019.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hydrangea* plant named 'HIRIV', characterized by its upright and broadly spreading plant habit; freely branching habit; strong and sturdy stems; freely and continuous flowering habit; large and dense inflorescences with light red purple-colored sterile flowers; and good post-production longevity.

2 Drawing Sheets

Figure 1:
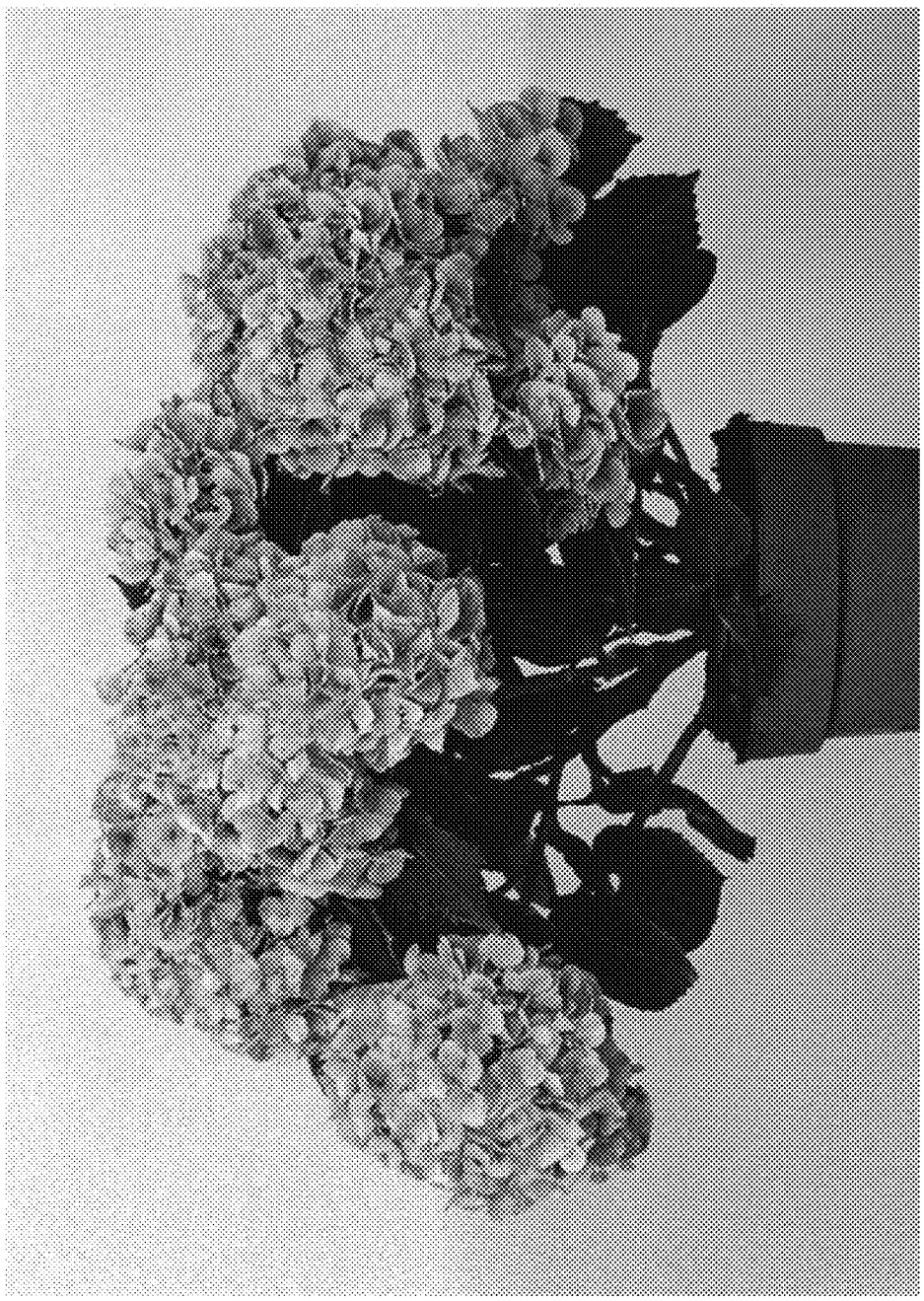

Botanical designation: *Hydrangea macrophylla.*
Cultivar denomination: 'HIRIV'.

CROSS-REFERENCED TO CLOSELY-RELATE APPLICATIONS

Title: *Hydrangea* Plant Named 'HIMOU'
Applicant: Roy Robin van Dijk
Filed: Concurrently with the instant application

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIRIV'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in April, 2013 of a proprietary selection of *Hydrangea macrophylla* identified as code number 1011, not patented, as the female, or seed, parent with a proprietary selection of *Hydrangea macrophylla* identified as code number 1004, not patented, as the male, or pollen, parent. The new *Hydrangea* plant was discovered and selected as a single flowering plant from within the progeny of the stated cross-pollination in a controlled greenhouse environment in De Lier, The Netherlands in April, 2015.

Asexual reproduction of the new *Hydrangea* plant by terminal vegetative cuttings since June, 2015 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIRIV'. These characteristics in combination distinguish 'HIRIV' as a new and distinct *Hydrangea* plant:

1. Upright and broadly spreading plant habit.
2. Freely branching habit.
3. Strong and sturdy stems.
4. Freely and continuous flowering habit.
5. Large and dense inflorescences with light red purple-colored sterile flowers.
6. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* are sturdier than plants of the female parent selection.
2. Plants of the new *Hydrangea* flower for a longer period of time than plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* are sturdier than plants of the male parent selection.

2. Plants of the new *Hydrangea* have longer postproduction longevity than plants of the male parent selection.

Plants of the new *Hydrangea* can be compared to plants of *Hydrangea macrophylla* 'HIMOU', disclosed in a U.S. Plant Patent application filed concurrently. Plants of the new *Hydrangea* differ primarily from plants of 'HIMOU' in the following characteristics:

1. Plants of the new *Hydrangea* are smaller than plants of 'HIMOU'.
2. Plants of the new *Hydrangea* have broader inflorescences with more sterile flowers than plants of 'HIMOU'.

Plants of the new *Hydrangea* can also be compared to plants of *Hydrangea macrophylla* 'Early Pink', not patented. In side-by-side comparisons, plants of the new *Hydrangea* differed primarily from plants of 'Early Pink' in the following characteristics:

1. Stems of plants of the new *Hydrangea* are sturdier than stems of plants of 'Early Pink'.
2. Sterile flowers of plants of the new *Hydrangea* are sturdier than sterile flowers of plants of 'Early Pink'.
3. Sterile flowers of plants of the new *Hydrangea* are more cupped than sterile flowers of plants of 'Early Pink'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'HIRIV' grown in a container.

Figure 2:
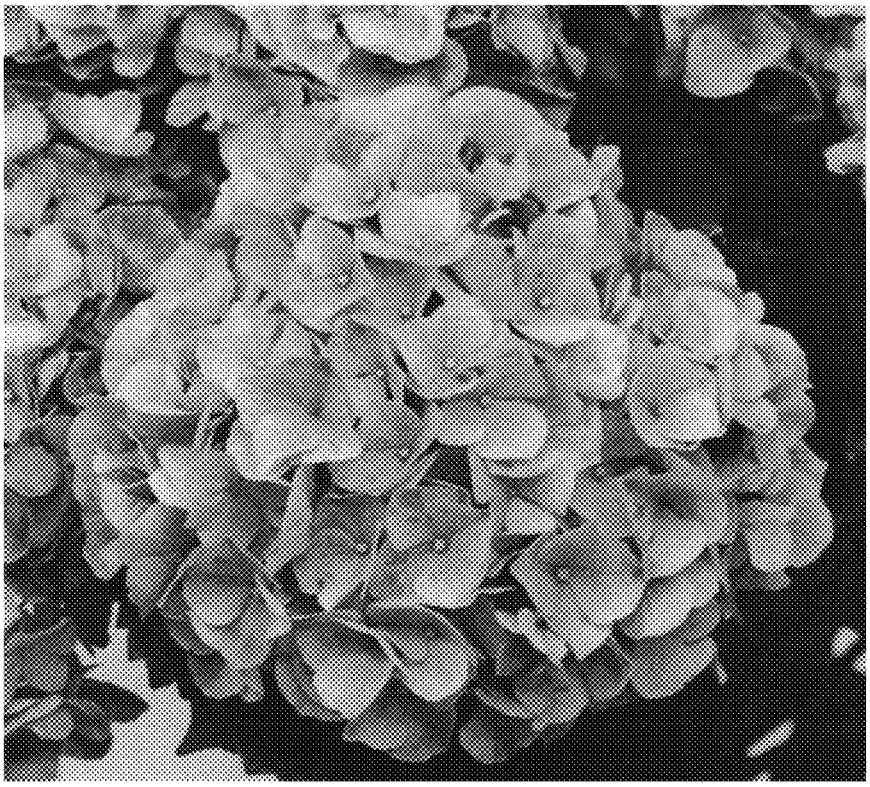

The photograph on the second sheet (FIG. 2 of 2) is a close-up view of a typical inflorescence of 'HIRIV'.

DETAILED BOTANICAL DESCRIPTION

Plants used in the aforementioned photographs and in the following description were grown during the autumn in 13-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and lightly levels were about 4,000 lux. Plants of the new *Hydrangea* were pinched one time and were two years old when the photographs and description were taken. In the following description, color references are made to The Royal Horticultural Society Colour Chart, 2015 Edition, except where general terms of ordinary dictionary significance are used. Plants are not typically "blued" (treated with aluminum sulfate).

Botanical description: *Hydrangea macrophylla* 'HIRIV'.

Parentage:

*Female, or seed, patent*.—Proprietary selection of *Hydrangea macrophylla* identified as code number 1011, not patented.

*Male, or pollen, patent*.—Proprietary selection of *Hydrangea macrophylla* identified as code number 1004, not patented.

Propagation:

*Type cutting*.—By vegetative terminal cuttings.

*Time to initiate roots, summer*.—About twelve days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About one month at temperatures about 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular in overall shape; strong and sturdy stems; moderately vigorous growth habit and moderate growth rate; about six months from propagation are required to produce a finished flowering plant.

*Plant height*.—About 28.5 cm.

*Plant diameter or area of spread*.—About 46.1 cm.

Lateral branch description:

*Branching habit*.—Freely branching habit with about 13 lateral branches per plant; pinching enhances lateral branch development.

*Length*.—About 13.6 cm.

*Diameter*.—About 5.5 mm.

*Internode length*.—About 4.1 cm.

*Strength*.—Strong, sturdy.

*Aspect*.—About 60° from vertical.

*Texture*.—Smooth, glabrous; fully developed, woody.

*Luster*.—Moderately glossy.

*Color, developing*.—Close to 144A to 144B.

*Color, fully developed*.—Close to 199A and N199C.

*Lenticels*.—Density: Medium. Length: About 2.5 mm. Width: About 0.5 mm. Color: Close to between N186C and 200C.

Leaf description:

*Arrangement*.—Opposite, simple.

*Length*.—About 9.1 cm.

*Width*.—About 7.7 cm.

*Shape*.—Broadly ovate.

*Apex*.—Short apiculate.

*Base*.—Short attenuate.

*Margin*.—Coarsely serrate.

*Texture and luster, upper surface*.—Slightly rugose, glabrous; semi-glossy.

*Texture and luster, lower surface*.—Moderately rugose, glabrous; slightly glossy.

*Venation pattern*.—Pinnate.

*Color*.—Developing leaves, upper surface: Close to 137A. Developing leaves, lower surface: Close to between 144A and 146B. Fully developed leaves, upper surface: Close to NN137A; venation, close to 144A to 144B. Fully developed leaves, lower surface: Close to 147B; venation, close to 147C.

*Petioles*.—Length: About 2.4 cm. Diameter: About 5 mm. Texture and luster, upper surface: Smooth, glabrous; slightly glossy. Texture and luster, lower surface: Smooth, glabrous; moderately glossy. Color, upper and lower surfaces: Close to between 144A and 146C.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly and slightly drooping and fertile flowers mostly upright.

*Fragrance*.—None detected.

*Natural flowering season*.—In the garden, plants flower continuously from the late spring to late summer in The Netherlands; flower dormancy can be broken by giving a two-month cold treatment.

*Flower longevity*.—Good postproduction longevity; sterile flowers maintain good substance for about six weeks on the plant, sterile flowers persistent; fertile flowers last about one week on the plant, fertile flowers not persistent.

*Quantity of flowers*.—Freely flowering habit; about 400 sterile flowers per panicle and about 80 fertile flowers per panicle.

*Panicle height*.—About 8.7 cm.

*Panicle diameter*.—About 14.8 cm.

*Sterile flower buds*.—Length: About 8 mm. Diameter: About 1.4 cm. Shape: Broad cup-shaped. Color: Close to 145A to 145C; proximally, tinged with close to 65A.

*Fertile flower buds*.—Length: About 2 mm. Diameter: About 2 mm. Shape: Globular. Color: Close to 145C to 145D.

*Sterile flower diameter*.—About 2.7 cm.

*Sterile flower depth* (*height*).—About 9 mm.

*Fertile flower diameter*.—About 3.5 mm.

*Fertile flower depth* (*height*).—About 3 mm.

*Petals, sterile flowers*.—Quantity and arrangement: Four in a single whorl. Length: About 1.5 mm. Width: About 1 mm. Shape: Broadly ovate, concave. Apex: Acute. Base: Cuneate. Margin: Entire. Texture and luster, upper and lower surfaces: Smooth, glabrous; matte. Color: When opening and fully opened, upper surface: Lighter than 65D; color does not change with development. When opening and fully opened, lower surface: Close to 65C to 65D; color does not change with development.

*Petals, fertile flowers*.—Quantity and arrangement: Five in a single whorl. Length: About 2 mm. Width: About 1 mm. Shape: Ovate, concave. Apex: Acute. Base: Cuneate. Margin: Entire. Texture and luster, upper and lower surfaces: Smooth, glabrous; matte. Color: When opening and fully opened, upper surface: Lighter than 65D; color does not change with development. When opening and fully opened, lower surface: Close to 145D slightly ringed with lighter than 65D; color does not change with development.

*Sepals, sterile flowers*.—Quantity and arrangement: Typically four, occasionally three, five or six, in a single whorl. Length: About 1.4 cm. Width: About 1.7 cm. Shape: Broadly rhomboidal to roughly deltoid. Apex: Broad and bluntly acute. Base: Cuneate. Margin: Entire to slightly serrate; slightly and coarsely undulate. Texture and luster, upper and lower surfaces: Smooth, glabrous; matte. Color: When opening, upper surface: Close to 73B. When opening, lower surface: Close to between 73B and 75C; proximally, close to 73A. Fully opened, upper surface: Close to 75C; distally, close to 68B; slightly and irregularly blotched with close to 145A; with development, color becoming closer to 65A strongly blotched with 143B, 144A, 145A to 145B and 154C to 154D. Fully opened, lower surface: Close to 75C; proximally, close to 68B; slightly and irregularly blotched with close to 145B; with development, color becoming closer to 73D strongly blotched with close to 145A, 146D and 147D.

*Sepals, fertile flowers*.—Quantity and arrangement: Five in a single whorl. Length: About 1.5 mm. Width: About 1 mm. Shape: Ovate. Apex: Acute. Base: Broadly cuneate. Margin: Entire. Texture and luster, upper and lower surfaces: Smooth, glabrous; matte. Color: When opening, upper and lower surfaces: Close to 144B. Fully opened, upper and lower surfaces: Close to 144B; color does not change with development.

*Pedicels, sterile flowers*.—Length: About 1.7 cm. Diameter: About 1.5 mm. Strength: Moderately strong. Aspect: About 30° from peduncle. Texture and luster: Densely pubescent; matte. Color: Close to 65A; proximally, close to 146D.

*Pedicels, fertile flowers*.—Length: About 4 mm. Diameter: About 1 mm. Strength: Moderately strong. Aspect: About 10° from peduncle. Texture and luster: Moderately pubescent; matte. Color: Close to 152D.

*Reproductive organs, sterile flowers*.—Stamens: Quantity per flower: Eight. Filament length: About 0.5 mm. Filament color: Close to 156D. Anther shape: Broadly oblong. Anther length: About 0.5 mm. Anther color: Close to 156A. Pollen amount: None detected. Pistils: Pistil quantity per flower: Two. Pistil length: About 0.75 mm. Stigma shape: Club-shaped. Stigma color: Close to 157D. Style length: About 0.5 mm. Style color: Close to 157D. Ovary color: Close to 145C.

*Reproductive organs, fertile flowers*.—Stamens: Quantity per flower: Eight. Filament length: About 0.5 mm. Filament color: Close to 156D. Anther shape: Broadly oblong. Anther length: About 0.5 mm. Anther color: Close to 156A. Pollen amount: None observed. Pistils: Pistil quantity per flower: Two. Pistil length: About 0.75 mm. Stigma shape: Club-shaped. Stigma color: Close to 157D. Style length: About 0.5 mm. Style color: Close to 157D. Ovary color: Close to 145C.

*Seeds*.—To date, seed development has not been observed on plants of the new *Hydrangea*.

Pathogen & pest resistance: Under commercial production conditions, plants of the new *Hydrangea* have been observed to tolerate Powdery Mildew (*Erysiphe friesii* var. *friesii*) and *Botrytis* (*Botrytis cinerea*). Plants of the new *Hydrangea* not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIRIV' as illustrated and described.

* * * * *